(12) United States Patent
Bäck et al.

(10) Patent No.: US 8,815,037 B2
(45) Date of Patent: Aug. 26, 2014

(54) METHOD OF MANUFACTURING ABSORBENT ARTICLES, APPARATUS FOR MANUFACTURING ABSORBENT ARTICLES AND DISPOSABLE PANT

(75) Inventors: Lucas Bäck, Billdal (SE); Lennart Nilsson, Skärhamn (SE)

(73) Assignee: SCA Hygiene Products AB, Göteborg (SE)

( * ) Notice: Subject to any disclaimer, the term of this patent is extended or adjusted under 35 U.S.C. 154(b) by 126 days.

(21) Appl. No.: 13/578,459

(22) PCT Filed: Feb. 16, 2010

(86) PCT No.: PCT/EP2010/051899
§ 371 (c)(1),
(2), (4) Date: Sep. 10, 2012

(87) PCT Pub. No.: WO2011/101018
PCT Pub. Date: Aug. 25, 2011

(65) Prior Publication Data
US 2012/0324633 A1    Dec. 27, 2012

(51) Int. Cl.
*A61F 13/15* (2006.01)
*A61F 13/496* (2006.01)
*B29C 65/00* (2006.01)

(52) U.S. Cl.
CPC ....... *A61F 13/4963* (2013.01); *A61F 13/15739* (2013.01); *A61F 13/15747* (2013.01); *B29C 66/0324* (2013.01)
USPC ........... 156/204; 156/202; 156/226; 156/227; 493/405; 493/409

(58) Field of Classification Search
CPC ........... A61F 13/4963; A61F 13/15739; A61F 13/15747; B29C 66/0324
USPC ........... 156/202, 204, 226, 227; 493/405, 409
See application file for complete search history.

(56) References Cited

U.S. PATENT DOCUMENTS

| 5,074,854 A | 12/1991 | Davis |
| 5,662,638 A | 9/1997 | Johnson et al. |

(Continued)

FOREIGN PATENT DOCUMENTS

| EP | 1 600 067 A1 | 11/2005 |
| EP | 1 792 594 A1 | 6/2007 |

(Continued)

OTHER PUBLICATIONS

International Search Report (PCT/ISA/210) issued on Sep. 29, 2010, by the European Patent Office as the International Searching Authority for International Application No. PCT/EP2010/051899.

(Continued)

*Primary Examiner* — Michael Orlando
*Assistant Examiner* — Marta Dulko
(74) *Attorney, Agent, or Firm* — Buchanan Ingersoll & Rooney PC

(57) ABSTRACT

A method of manufacturing absorbent articles (9) includes feeding a longitudinal web (1) of web material having openings (16) such that spaced apart, opposing margins (18) of web material are formed between the respective opening and opposing longitudinal edges of the web material; carrying out a folding action (20) of folding the web about itself along its longitudinal direction; carrying out a second (30) folding action of folding at least a portion of the web along its longitudinal direction; after the second folding action, forming a joint (46) in the web, the joint being formed at least in a part of the region in which the opposing margins have been brought together by the second folding action; finally separating (8) the web through the joint to separate an individual absorbent article from the end of the web.

11 Claims, 17 Drawing Sheets

(56) References Cited

U.S. PATENT DOCUMENTS

| | | | |
|---|---|---|---|
| 6,042,673 A | 3/2000 | Johnson et al. | |
| 6,277,223 B1 * | 8/2001 | Herrin et al. | 156/73.1 |
| 6,497,696 B1 | 12/2002 | Freiburger et al. | |
| 7,052,485 B2 | 5/2006 | Suzuki | |
| 7,806,884 B2 | 10/2010 | Hildeberg et al. | |
| 7,931,636 B2 * | 4/2011 | LaVon et al. | 604/385.28 |
| 8,551,064 B2 * | 10/2013 | LaVon et al. | 604/385.04 |
| 8,672,914 B2 * | 3/2014 | Ashton et al. | 604/392 |
| 2003/0217803 A1 * | 11/2003 | Hermansson et al. | 156/204 |
| 2005/0027274 A1 * | 2/2005 | Suzuki et al. | 604/385.01 |
| 2005/0148974 A1 * | 7/2005 | Datta et al. | 604/385.01 |
| 2006/0042746 A1 | 3/2006 | Ukegawa | |
| 2006/0047260 A1 * | 3/2006 | Ashton et al. | 604/396 |
| 2006/0174400 A1 | 8/2006 | Kurata | |
| 2008/0134487 A1 * | 6/2008 | Hartono | 29/428 |
| 2010/0018637 A1 | 1/2010 | Otsubo | |

FOREIGN PATENT DOCUMENTS

| | | |
|---|---|---|
| EP | 2 106 771 A1 | 10/2009 |
| JP | H06-500153 A | 1/1994 |
| JP | 07-075653 A | 3/1995 |
| JP | H11-513295 A | 11/1999 |
| JP | 2001527449 A | 12/2001 |
| JP | 2006095277 A | 4/2006 |
| JP | 2006-515528 A | 6/2006 |
| JP | 2008-168011 A | 7/2008 |
| JP | 2010-029279 A | 2/2010 |
| RU | 2007-102071 A | 7/2008 |
| WO | 98/51252 A1 | 11/1998 |
| WO | 2004/062398 A1 | 7/2004 |
| WO | WO 2004/062541 A1 | 7/2004 |
| WO | WO 2004062541 A1 * | 7/2004 |

OTHER PUBLICATIONS

International Preliminary Report on Patentability (PCT/IPEA/409) issued on Feb. 8, 2012, by the European Patent Office for International Application No. PCT/EP2010/051899.

Office Action (Notice of Reasons for Rejection) issued on Feb. 3, 2014, by the Japanese Patent Office in corresponding Japanese Patent Application No. 2012-552270, and an English Translation of the Office Action (10 pages).

Office Action (Decision on Grant) issued on Jan. 30, 2014, by the Russian Patent Office in corresponding Russian Patent Application No. 2012134068, and an English Translation of the Office Action (15 pages).

* cited by examiner

METHOD OF MANUFACTURING ABSORBENT ARTICLES, APPARATUS FOR MANUFACTURING ABSORBENT ARTICLES AND DISPOSABLE PANT

TECHNICAL FIELD

The present invention pertains to a method of manufacturing absorbent articles, in particular a method of manufacturing disposable diaper pants or disposable incontinence pants, an apparatus for manufacturing an absorbent article as well as a disposable diaper or incontinence pant.

TECHNOLOGICAL BACKGROUND

Disposable pants for diapers or for incontinence products are well-known products. For these, it has always been an aim to equip them with a garment-like appearance, such that the diapers or incontinence products, when worn by a user, have the outer appearance of a conventional pant, in particular the appearance of conventional underwear/undergarments.

One of the issues when mass-producing disposable pants of this type is the appearance of the portion at which the front portion and the rear portion are joined together at the sides. When producing a seam of this kind, the typical issue that arises is that the seam and any flange portion that inevitably is produced, sticks out to the outside if the pants are worn by a user.

In order to improve the garment-like appearance of these disposable pants, it is an aim that the side seam and the resulting flange material does not stick out to the sides of the pants but that these seams are not really visible on the outside.

Several attempts to achieve this have been carried out. WO 2004/062541 A1, for example, discloses a method of producing diaper pants of disposable type, wherein the weld seams at the sides are made such that the front portion and the rear portion overlap in a manner such that the inner layer of the front portion is welded to the outer layer of the rear portion. The resulting pant has a garment-like appearance but the method requires advanced and difficult handling of the diapers at the welding step.

U.S. Pat. No. 6,042,673 discloses a method of making a flangeless seam for a disposable pant, wherein the step of actually making the seam requires several complicated folding steps.

U.S. Pat. No. 5,074,854 discloses a disposable undergarment having additional break-away panels which connect the front portion and the rear portion along seams. The manufacturing process is likewise complicated.

SUMMARY OF THE INVENTION

Starting from the technological background given above, it is an object of the present invention to provide a method of manufacturing absorbent articles, an apparatus for manufacturing absorbent articles as well as a disposable diaper or incontinence pant which allow for an improved and efficient manufacturing process.

In claim 1, a method to achieve the above object is provided. Accordingly, the method of manufacturing absorbent articles comprises the steps of feeding a longitudinal web of web material, the web having two opposing longitudinal edges, a first side and a second side, the web furthermore having openings situated between the two opposing longitudinal edges, the openings being spaced apart from one another in the longitudinal direction of the web such that spaced apart, opposing margins of web material are formed between the respective opening and the opposing longitudinal edges of the web material. A first folding action of folding the web about itself along its longitudinal direction such that portions of the first side of the web face each other is carried out and a second folding action of folding at least a portion of the web along its longitudinal direction to bring together the opposing margins of web material such that they face each other on the second side of the web is carried out. After the second folding action, a joint is formed in the web, the joint being formed at least in a part of the region in which the opposing margins have been brought together by the second folding action, the joint extending between the longitudinal edges and the opening in the web. Finally, the web is separated through the joint to separate an individual absorbent article from the end of the web.

The method has the advantage that disposable pants, in particular diaper or incontinence pants, can be manufactured in which the joint between the layers of material and the resulting flange material is at least in its main portion turned towards the inside of the final product because the joint is formed at the two second sides of the web. In other words, the side seams as well as the resulting flange material are turned to the inside of the final absorbent article. By means of the succession of the folding steps, the production can be carried out in a continuous process at high speed.

In order to support the final turning of the product, and in particular of the seams, into its intended positioning with the first side inside and the second side outside, the method after forming the joint preferably further comprises the step of pre-separating the web in the region where the joint is formed while leaving at least a portion of the margins unaffected to maintain the web integrity along its longitudinal direction, the unaffected portion of the margins preferably extending towards the longitudinal edges.

Preferably, the method further comprises the step of carrying out a third folding action of at least partially reversing the second folding action such that at least portions of the web folded in the second folding action face each other on the first side of the web, before separating the web. By means of the third folding action, the product can be turned back into its intended positioning with the first side inside and the second side outside of the product, wherein the joint is then mainly situated inside the final product. In other words, the side seams as well as the resulting flange material are situated inside of the final absorbent article such that the visual and haptic appearance of the final absorbent article becomes more garment-like.

Preferably, a further step is carried out of holding the web when carrying out the third folding action. There are different options for holding the web when carrying out the third folding action. In particular, the web can be held at two portions of the web corresponding to two consecutive joints of the web, or it can be held at a leading joint or a following joint, seen in the direction of web feed, while carrying out the third folding action.

The first folding action can be carried out efficiently either by folding the web in the first folding action substantially about its longitudinal center line, or by folding the web in the first folding action substantially about a folding line which is offset from its longitudinal center line.

In the second folding action, the web may be folded about a line which is spaced apart from the respective longitudinal edges of the web substantially by the width of the margin of the unfolded web. In combination with the first folding action, this leads to a substantially "M" cross-section of the folded web which enables an efficient joining process. Preferably, the two opposing longitudinal edges of the web are aligned with one another in or after the second folding step such that a high-quality product can be achieved.

In the second folding step, the two opposing portions may be folded in a phase-shifted manner, in particular sequentially, in order to avoid collision of the respective folding mechanisms.

To provide, in the final product, a seam which is as thin and flexible as possible, in the step of forming a joint, the joint may be provided in the form of two or more separate joining portions such that at each individually cut final product only one of the joining portions remains. Preferably, the two or more separate joining portions are formed simultaneously in the web material.

To be in a position to efficiently produce pants, before the first folding action, preferably a further step is carried out of providing the web with absorbent sections spaced apart in the longitudinal direction on the first side of the web, the absorbent section being situated between two respective openings.

An apparatus for carrying out the method described above is claimed in claim 13. Accordingly, the apparatus comprises feeding means for feeding a longitudinal web of web material along a machine direction, the web having two opposing longitudinal edges, a first side and a second side, the web furthermore having openings situated between the two opposing longitudinal edges, the openings being spaced apart from one another in the longitudinal direction of the web such that spaced apart, opposing margins of web material are formed between the respective opening and the opposing longitudinal edges of the web material. The apparatus further comprises a first folding means for carrying out a first folding action of folding the web about itself along its longitudinal direction such that portions of the first side of the web face each other and a second folding means for carrying out a second folding action of folding at least a portion of the web along its longitudinal direction to bring together the opposing margins of web material such that they face each other on the second side of the web. Furthermore, the apparatus comprises a joining means for forming a joint in the web, the joint being formed at least in a part of the region in which the opposing margins have been brought together by the second folding action, the joint extending between the longitudinal edges and the opening in the web, the joining means being situated downstream of the first and second folding means, and a separating means for separating the web at the joint to separate an individual absorbent article from the end of the web, the cutting means being situated downstream of the third folding means.

Preferably, a pre-separating means is provided to pre-separate the web in the region where the joint is formed, while leaving at least a portion of the margins unaffected to maintain the web integrity along its longitudinal direction, the pre-separating means being situated downstream of the joining means, wherein the unaffected portion of the margins preferably extends towards the longitudinal edges. The separation carried out by the pre-separation means may help to ease the turning of the final product into its intended orientation.

To turn the final product into its intended orientation, a third folding means may be provided for carrying out a third folding action of at least partially reversing the second folding action such that at least portions of the web folded in the second folding action face each other on the first side of the web, the third folding means being situated upstream of the separating means.

A reliable apparatus can be achieved if the first folding means is provided by a first guide which extends in the machine direction, the first guide being preferably provided in the form of a first guide bar, and/or if the second folding means is provided by a second guide which extends in the machine direction, the second guide being preferably provided by two parallel second guide bars which are spaced apart from one another. The same arrangement can also be used with respect to the third folding means, which can be provided in the form of a third guide extending in the machine direction, the third guide being preferably provided in the form of a third guide bar. Preferably, the third guide is provided integral with the first guide, and is preferably provided in the form of the first guide bar extending from an upstream position to carry out the first folding action, towards a downstream position, for carrying out the third folding action.

In order to further ease the turning of the product into its intended orientation, the apparatus further includes a holding means for holding the web when carrying out the third folding action, the holding means being arranged in the vicinity of the third folding means.

Preferably, the holding means is arranged to hold the web at two portions corresponding to two consecutive joints of the web when carrying out the third folding action.

Preferably, the holding means may be provided in the form of a polygonal wheel, the edges of the polygonal wheel being synchronised with the joining means such that the edges of the polygonal wheel contact the web substantially at the joints. Preferably, the holding means may also be provided in the form of an engaging mechanism, the engaging action of which is arranged to be synchronised with the joining means such that the engaging action takes place at the joints, the engaging mechanism being preferably provided in the form of clamps, fingers, paddles or of a belt pressing against fingers, paddles or corners of a polygonal wheel. In order to increase friction between the edges of the polygonal wheel and the web, the surfaces between the corners of the polygonal wheel are preferably concave. To securely hold the web to the wheel, the holding means is preferably provided with a vacuum means that is intended to hold at least a part of the web at the holding means. Of course, vacuum means can also be provided between the respective corners of the wheel in order to hold the remaining portion of the web closely to the wheel. This specific embodiment facilitates carrying out the third folding action because the vacuum sucks one side of the folded web towards the wheel and provides for a minute separation of the respective first sides of the web such that a gap is opened through which the web can be pass in the third folding action.

Disposable pants according to claim 26 are provided. The disposable pants include a longitudinal web of web material, the web having two opposing longitudinal edges, a first side and a second side. The web furthermore having openings situated between the two opposing longitudinal edges, the openings being spaced apart from one another in the longitudinal direction of the web such that spaced apart and two opposing margins of web material are formed between the respective opening and the opposing longitudinal edges of the web material. The two opposing margins being joined to one another at least in a part of the region of the opposing margins and the resulting seam being at least partially directed towards the inside of the disposable pants, wherein the largest lateral dimension of the opening being larger than two times the smallest lateral dimension of the smallest margin.

A disposable pant of this type has the advantage that it has a garment-like feel and appearance and it can be effectively produced by means of the method and/or apparatus described above.

BRIEF DESCRIPTION OF THE DRAWINGS

In the following, embodiments of the apparatus for and the method of manufacturing absorbent articles are disclosed in the attached Figures, in which.

DETAILED DESCRIPTION OF THE PREFERRED EMBODIMENTS

Figure 1:
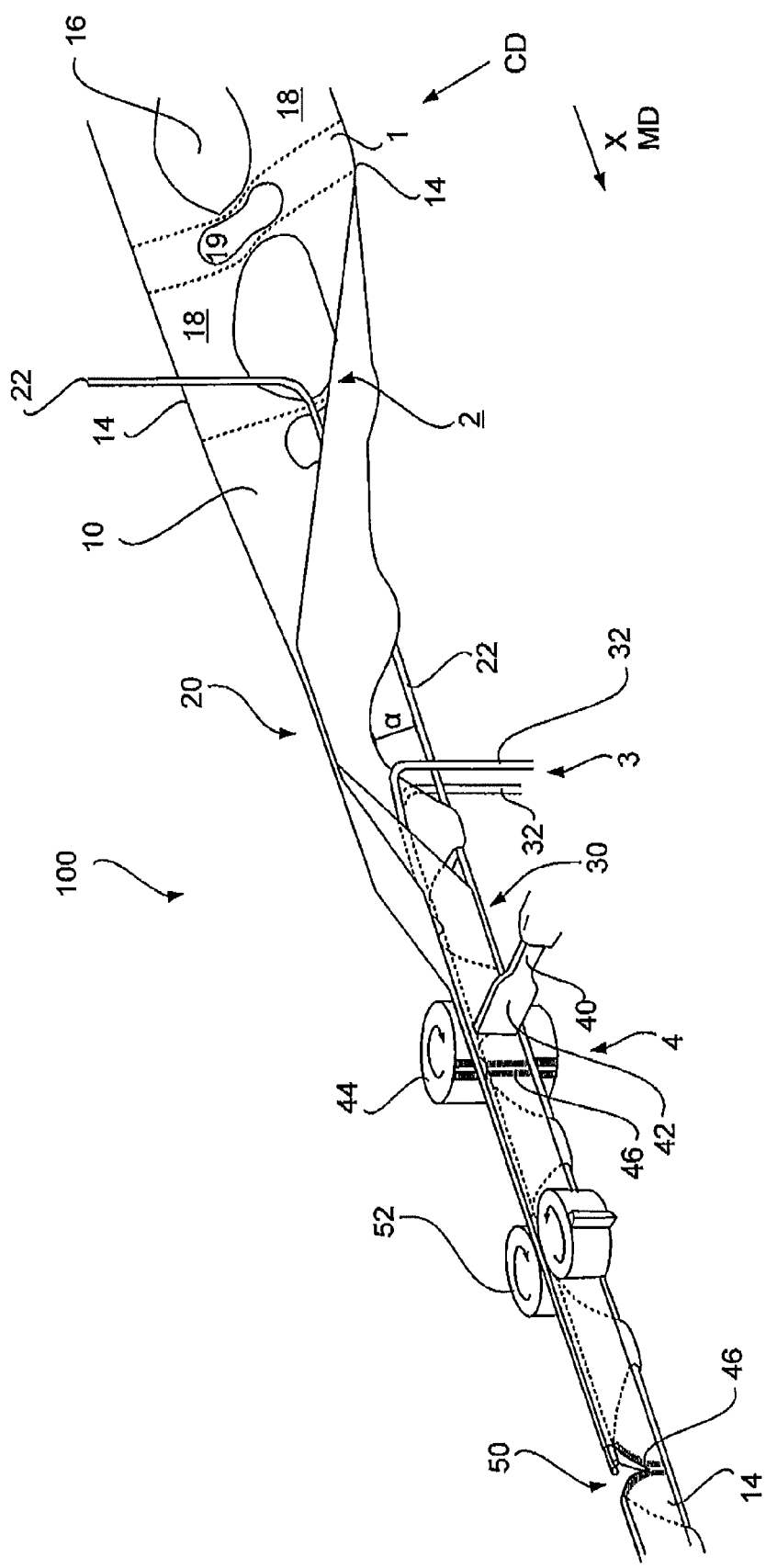
FIG. 1 shows a first portion of an apparatus of a first embodiment.

In the following, preferred embodiments of the present disclosure will be described by means of reference to the attached Figures. In the Figures, like or same elements will be denoted by the same reference numerals and repeated description thereof may be omitted in order to avoid redundancies.

FIG. 1 shows a first, upstream, portion of a manufacturing apparatus 100 according to the present disclosure, which is intended to manufacture absorbent articles, and, in particular, disposable diaper pants and/or incontinence pants.

A longitudinal web of web material 1 is fed along the feeding direction X, which is also the machine direction MD. The web 1 has a first side 10 and a second side 12. The web 1 comprises two opposing longitudinal edges 14 and is provided with openings 16 which are spaced apart from one another and which are provided fully inside the boundaries provided by the web of material 1. Between the openings 16 and the two longitudinal edges 14, opposing margins 18 of web material are present. The margins are intended to be defined in the area between the dotted lines, i.e. the margins extend in a cross-machine direction CD between any portion of the opening 16 and the respective longitudinal edge 14 of the web 1.

An absorbent core 19 is placed between two consecutive openings 16 in the web 1. The absorbent core may extend into the margins of web material.

A feeding means for feeding the web 1 is provided, which is, however, not shown in FIG. 1. The feeding means may be a roller from which the readily-manufactured web including the openings 16 and the absorbent cores 19 is unrolled. The feeding means may also be provided in any upstream station in the production process from which the web 1 with at least the selected features discussed above is fed to the apparatus 100.

After the feeding means, a first folding means 2 is provided, which carries out a first folding action of folding the web 1 about itself along its longitudinal direction X, such that portions of the first side 10 of the web material face each other. In the embodiment shown in FIG. 1, the web 1 is folded upon itself such that the two opposing longitudinal edges 14 are actually aligned with one another, as can be seen at reference numeral 20. However, this very specific alignment is not essential for the method.

The first folding means 2 is provided in the form of a guide bar 22, which extends, at least in its effective folding portion, along the feeding direction X and the machine direction MD of the apparatus 100. The first guide bar 22 provides a clear-cut edge or axis about which the web 1 can be folded lengthwise.

In addition to the first guide bar 22, a folding plough or folding boards are intended to be present, which are, however, not shown for clarity reasons in FIG. 1. The folding boards or the folding plough are intended to bring together the opposing edges 14 or, at least, the opposing margins 18 of the web 1 in the form as shown at reference numeral 20.

Downstream of the first folding means 2, a second folding means 3 is present, which affects a second folding action for folding at least a portion of the web 1 along its longitudinal direction to bring together the opposing margins of the web material, such that they face each other on the second side 12 of the web.

The readily-folded web, folded by the second folding means, can be seen at reference numeral 30. At this position, the folded web 1 has, substantially, an "M"-shape in cross-section. It is to be noted that the margins 18 can be and, preferably, are brought together directly at the position of reference numeral 30 and at the second side 12 of the web, because the openings 16 of the web 1 permit a direct contact of the two margins 18 at reference numeral 30.

The second folding means is provided by means of two second guide bars 32, which likewise extend along the feeding direction X and which are spaced apart from one another slightly in the plane defined by the unfolded web 1 and are spaced apart from the first guide bar 22 in the direction perpendicular to the unfolded web by a distance d in the height-direction in the Figure.

Distance d is set, in the embodiment of the apparatus shown in FIG. 1, such that the margins 18 can be brought together fully without the opposing longitudinal edges 14 touching the lower bar 22. Accordingly, the distance d is at least the distance of the smallest portion of the margin 18 plus the extension of the respective guide bars 22, 32.

A joining means 4 is present in order to form a joint in the web, wherein the joint is formed in at least a part of the region in which the opposing margins 18 have been brought together by the second folding action at the second folding means 3.

In the illustrated embodiment, the joint in the web 1 is provided in the web by means of an ultrasonic welding tool 40 having a welding horn 42, which fits between the first guide bar 22 and the second guide bar 32. Naturally, other joining means well-known in the art may be used. In the present case, the welding horn 42 enables welding the opposing margins 18 together. It is to be noted that the welding process takes place substantially through the opening 16 of the web 1, such that only the opposing margins 18 are welded together and, thus, only two layers of material are joined to one another.

The welding horn 42 works against a welding cylinder 44, which is synchronised with the web and in particular synchronised with the succession of the respective openings 16 in order to be in a position to produce a joint between the then to be cut individual absorbent articles.

Downstream of the joining means 4, a pre-separating means 5 for pre-separating the web in the region where the joint is formed is present. The pre-separating means 5 is provided in the form of rotating knives 50, which cut the web at the region where the joint 46 is provided in the web 1. As can be seen at reference numeral 50, the pre-separating step leads to a situation in which a part of the web is already pre-separated, but a portion of the joint 46 remains intact on both opposing portions of the cut. At the opposing longitudinal edge 14 of the web, at reference numeral 50, a small portion of the margin 18 remains unseparated, in order to maintain the web integrity along its longitudinal direction.

Furthermore, at reference numeral 50, the two second guide bars 32 terminate, such that the folds that were created at the second folding means 3 are no longer guided by the second guide bars 32. However, in other embodiments the second guide bars may also terminate in other sections of the apparatus such as directly after the first folding action or as late as immediately before the third folding action.

The first guide bar 22, however, remains and still guides the fold that was created at the first folding means 2.

Figure 2:
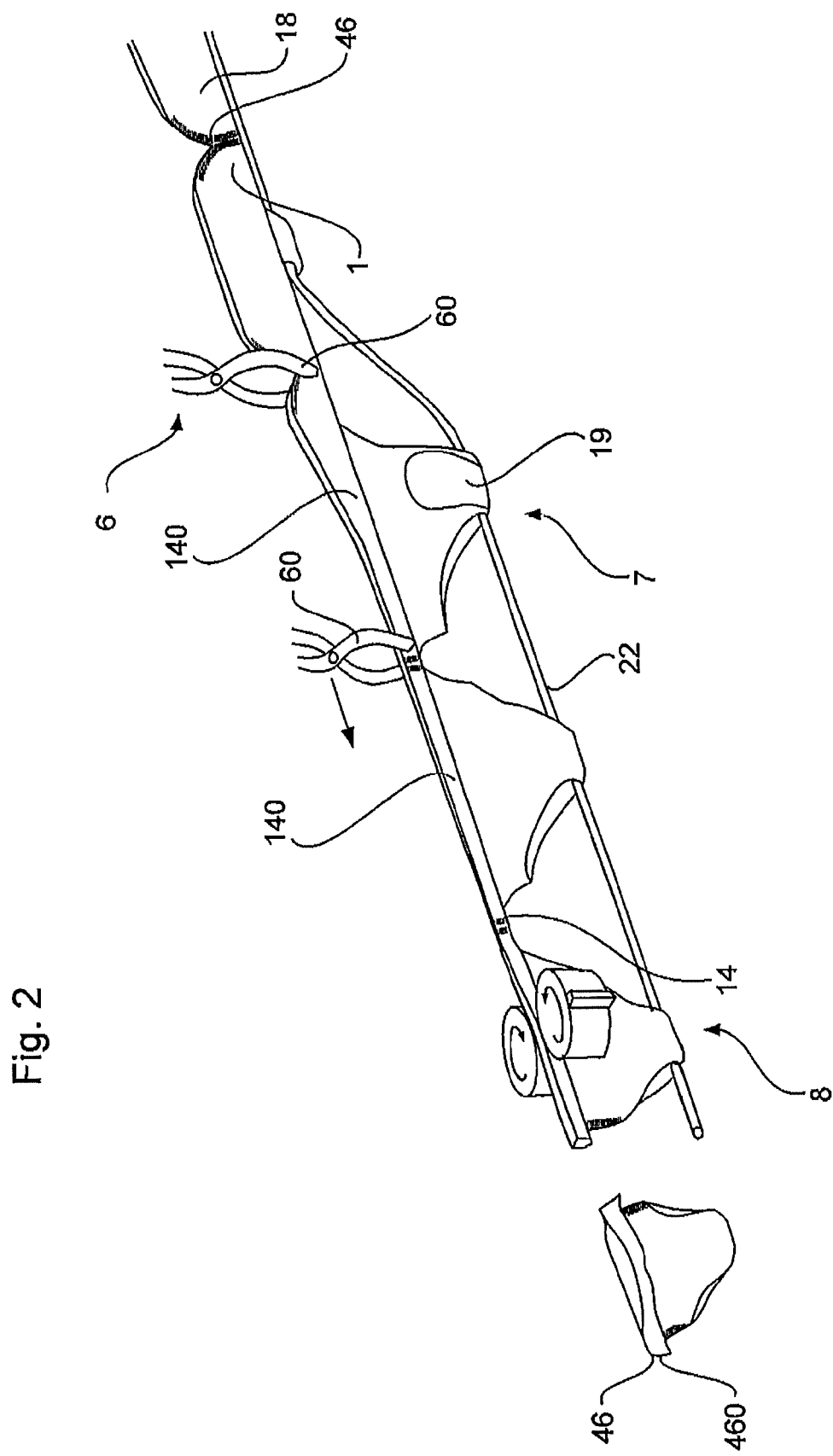
FIG. 2 shows a first alternative of a second portion of the apparatus of FIG. 1.

In FIG. 2, a first alternative of the process of unfolding the folds and turning the joined portion towards the inside of the final product is shown.

In particular, a holding means 6 is provided which is shown in FIG. 2 as a clamping means 60. The clamping means 60 grips the pre-cut web 1 at the respective consecutive joints 46 in the web 1 substantially at the waist band portion 140 of the folded web, such that a single individual absorbent article is clamped between two consecutive clamps 60.

A third folding means 7 is provided downstream of the holding process. The third folding means carries out an unfolding of a crotch section of the absorbent article provided with the absorbent core 19, such that the folding process that was carried out at the second folding means 3 is at least partially reversed. In particular, the region of the opposing margins 18 that were folded upon one another at the second folding means 3 are now folded back into an orientation in which the respective first sides 10 of the web face each other.

The third folding means 7 is provided, in FIG. 2, by means of the first guide bar 22, wherein the first guide bar 22 bends away downwardly, such that the crotch portion is pulled out of its M-folded configuration. At the opposing side edges 14, a waist band portion remains.

A separating means 8 is provided downstream of the third folding means 7, wherein the separating means 8 completely separates individual absorbent articles from the web.

As will be appreciated, the final absorbent product, which is preferably a disposable diaper pant or a disposable incontinence pant, has a structure in which the majority of the joint 46, which was provided at the joining means 4, is now located inside of the absorbent article. In particular, the majority of the flange material 460 remaining at the joint 46 is situated inside the final pants. The last small portion, which corresponds to a waist band portion, remains folded to the outside but can be likewise re-folded in order to achieve an absorbent article in which the entire joint, and in particular the flange resulting from the cutting action, is situated inside the absorbent article.

Figure 3:
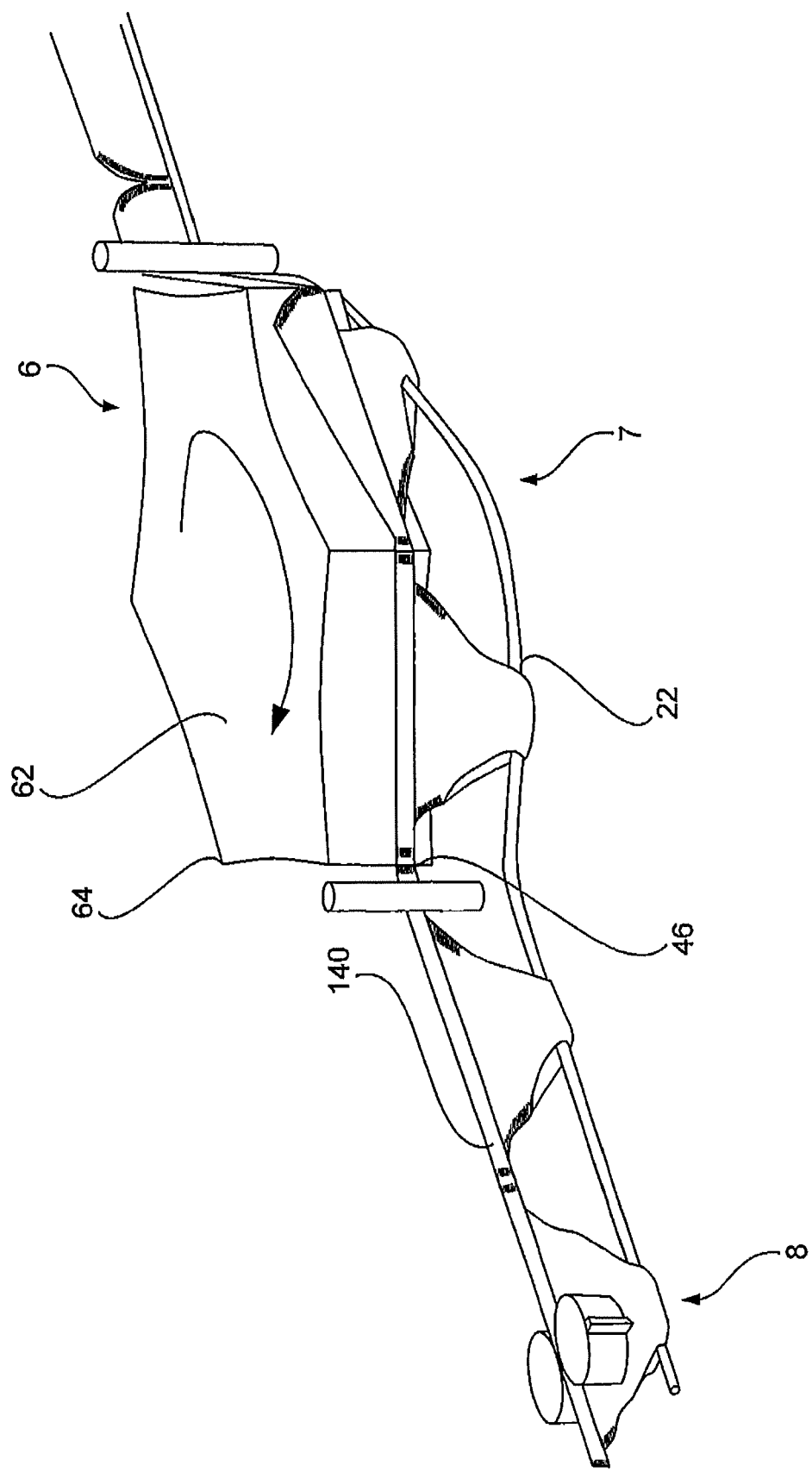
FIG. 3 shows a second alternative of the second portion of the apparatus of FIG. 1.

FIG. 3 shows an alternative to the clamps 60 of FIG. 2. The holding means 6 in FIG. 3 is provided in the form of a polygonal wheel 62, having corners 64. The polygonal wheel 62 has a length of each of the sides of the polygon which corresponds to a distance between two consecutive joints 46. Furthermore, the polygonal wheel 62 is synchronised with the joints such that each joint 46 of the web is associated with one of the corners 64 of the polygonal wheel. Preferably, the sides of the polygonal wheel between the corners 64 are slightly concave in order to increase the friction at the corners 64.

The polygonal wheel 62 is adapted to hold the respective absorbent article at the respective joints 46 during the third folding action. The third folding means 7 is shown in FIG. 3, again as the first guide bar, which bends away from the initial position in order to pull out the crotch portion of the absorbent article.

To support holding the web at the waist band portion 140, the polygonal wheel 62 may also be provided with vacuum means, either at the corners, between the corners or in a circumferential arrangement, such that the waist band portion 140 can by closely sucked to the wheel 62.

With reference to FIGS. 4 to 11, the method of manufacture is explained again in more detail.

Figure 4:
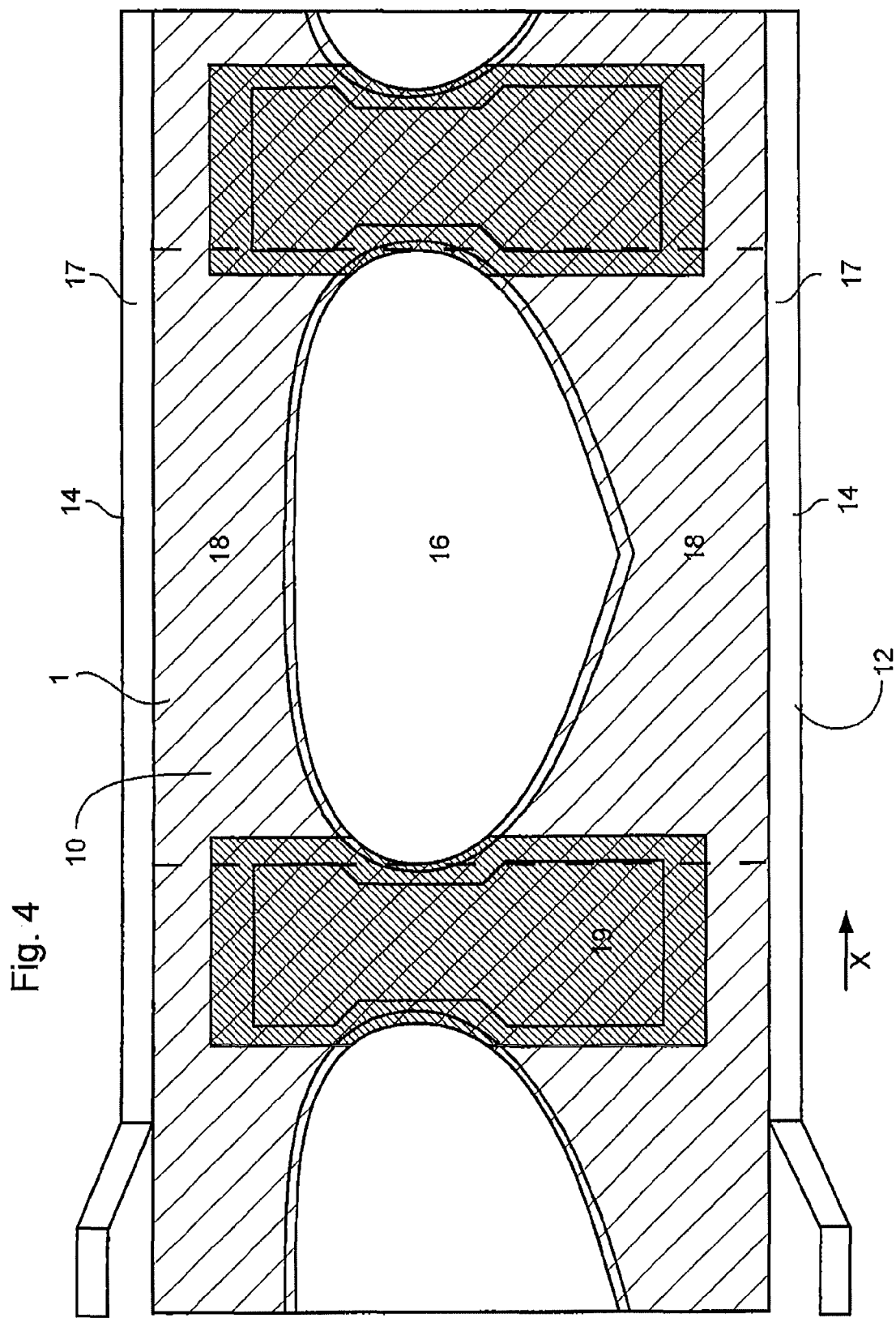
FIGS. 4 to 11 show schematically an embodiment of the method of manufacturing an absorbent article.

In particular, in FIG. 4, the web 1 with openings 16, absorbent cores 19, opposing side edges 14 and margins 18 is shown. Furthermore, a waist band section 17 is also shown in FIG. 4 and the feeding direction is, this time, from the left-hand side to the right-hand side along the direction indicated by arrow X.

Figure 5:
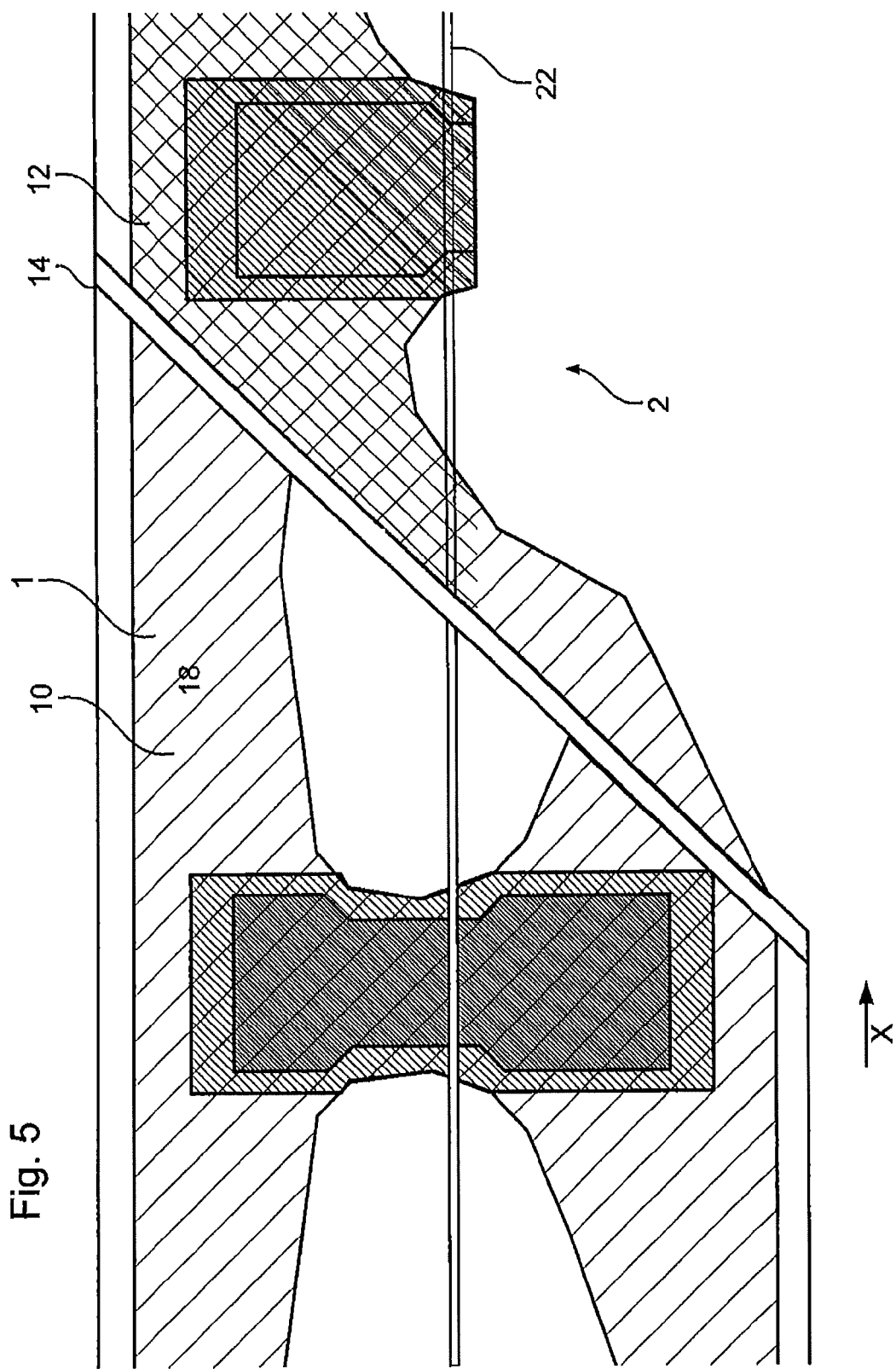

FIG. 5 shows a first folding action by means of a first guide bar 22, wherein the web 1 is folded lengthwise such that the opposing side edges 14 are brought together such that the margins 18 overlap at the first side 10 of the web.

Figure 6:
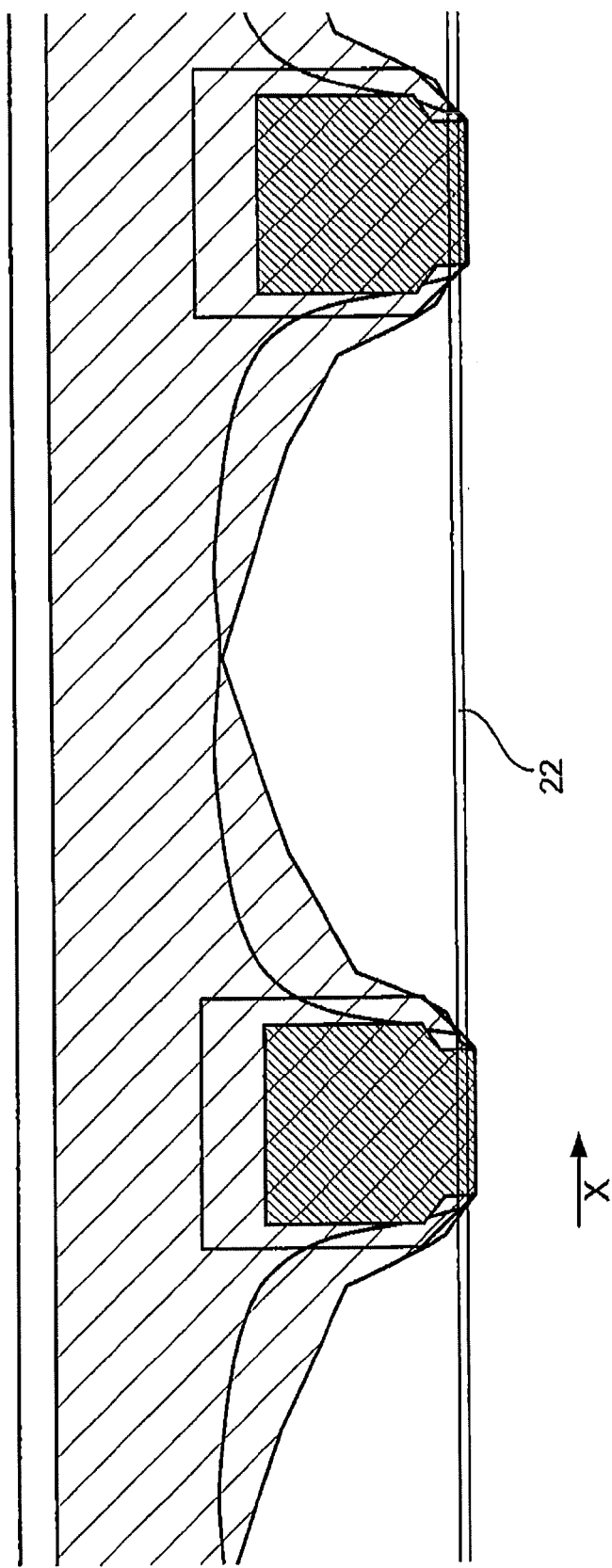

The then folded web as shown in FIG. 6 is to be carried along the feeding direction X.

Figure 7:
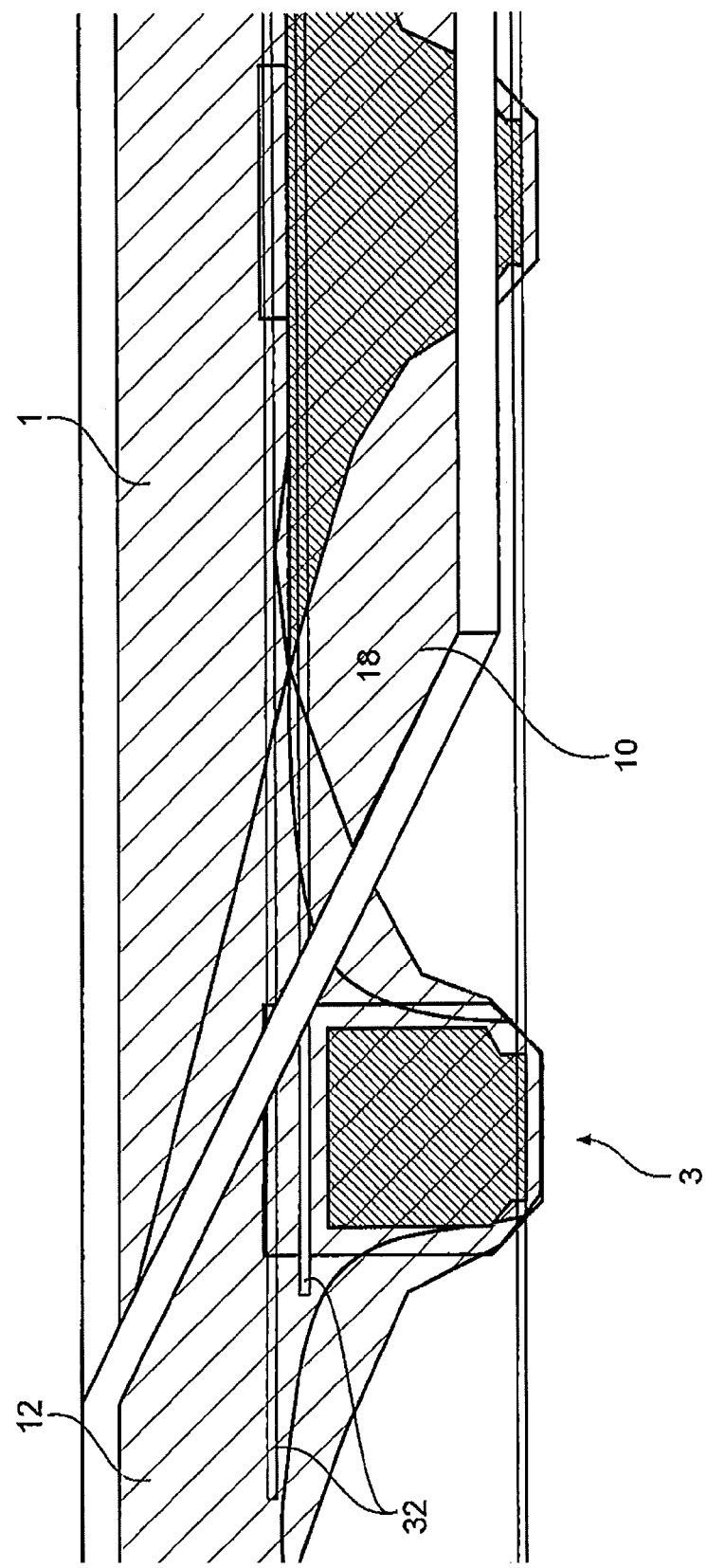
Figure 8:
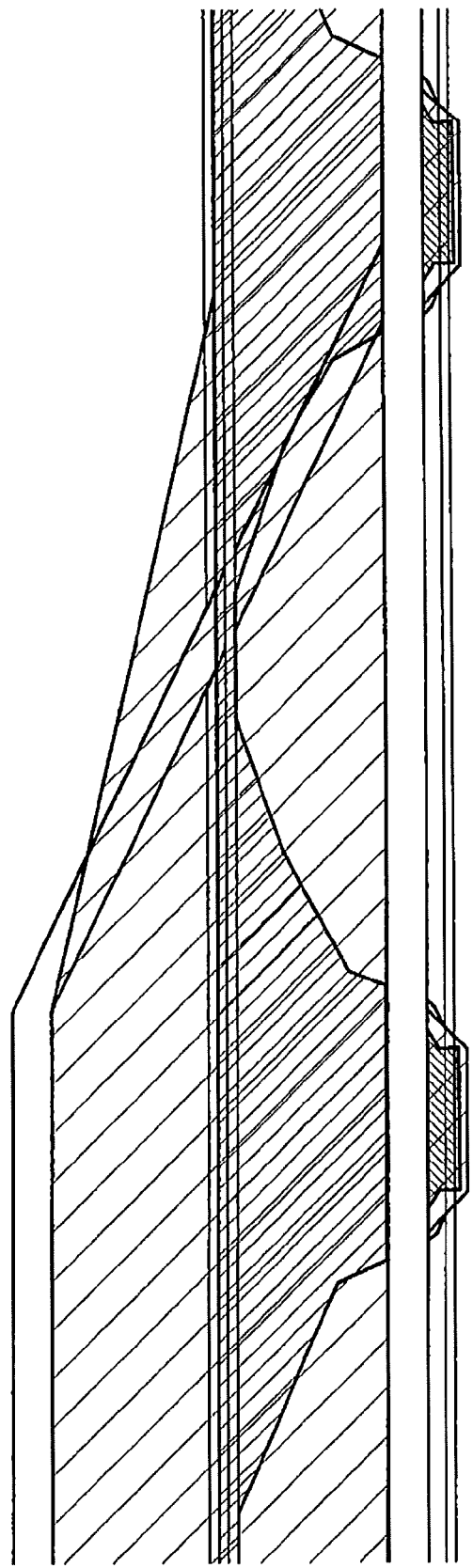

In FIG. 7, a second folding process at folding means 3 is shown, wherein second guide bars 32 are provided. As can be seen, the portions of the margins 18 are folded downwards again, about the edge provided by the second guide bars 32, wherein in FIG. 7 only the first portion of the web 1 is folded downwards and in FIG. 8 it is shown that also the other side of the web is folded downwards. In other words, the opposing portions of the web are folded sequentially.

Figure 9:
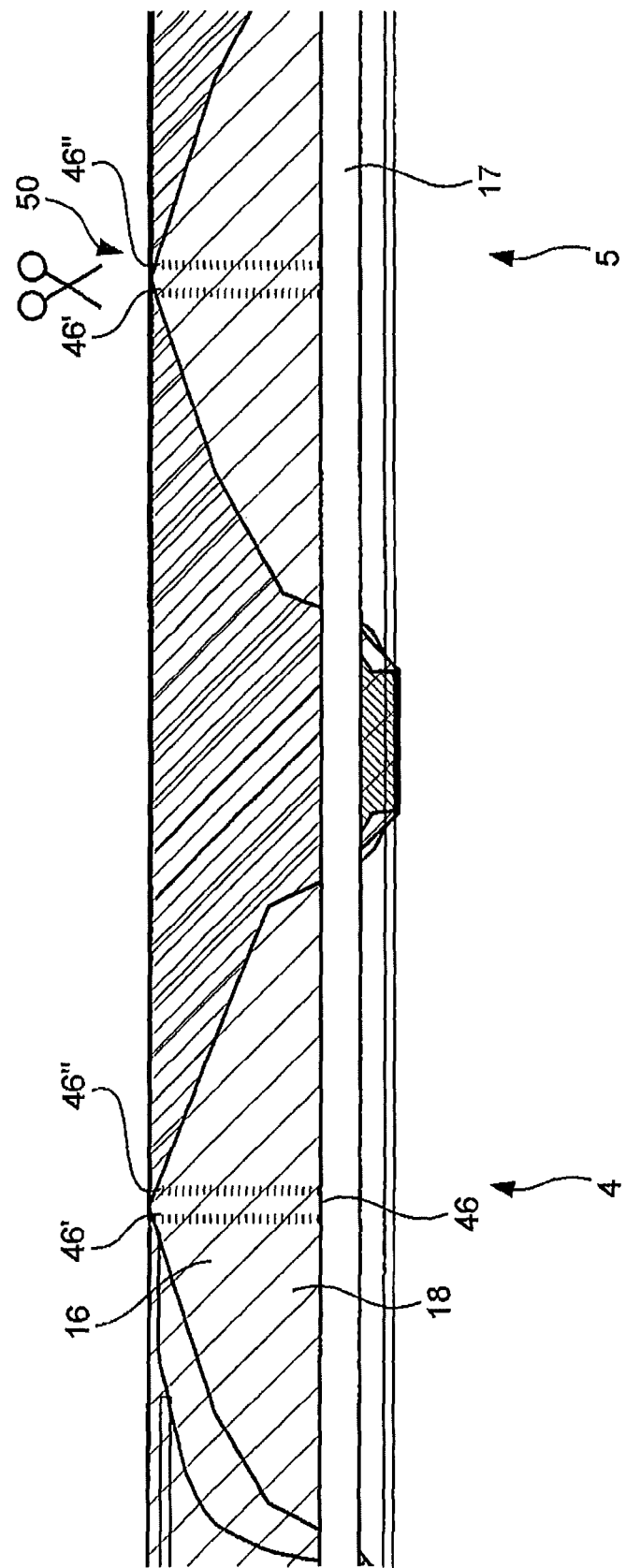

In FIG. 9, it is shown that the two margins 18 overlap through the openings 16 of the web and a joint 46 is formed at the joining means 4. The joint shown in FIG. 9 comprises of two separate seams 46' and 46", and in the pre-separation step 5, a cut is carried out between the first seam 46' and the second seam 46", however, leaving the waist band portion 17 unseparated, in order to maintain the structural integrity of the web.

Figure 10:
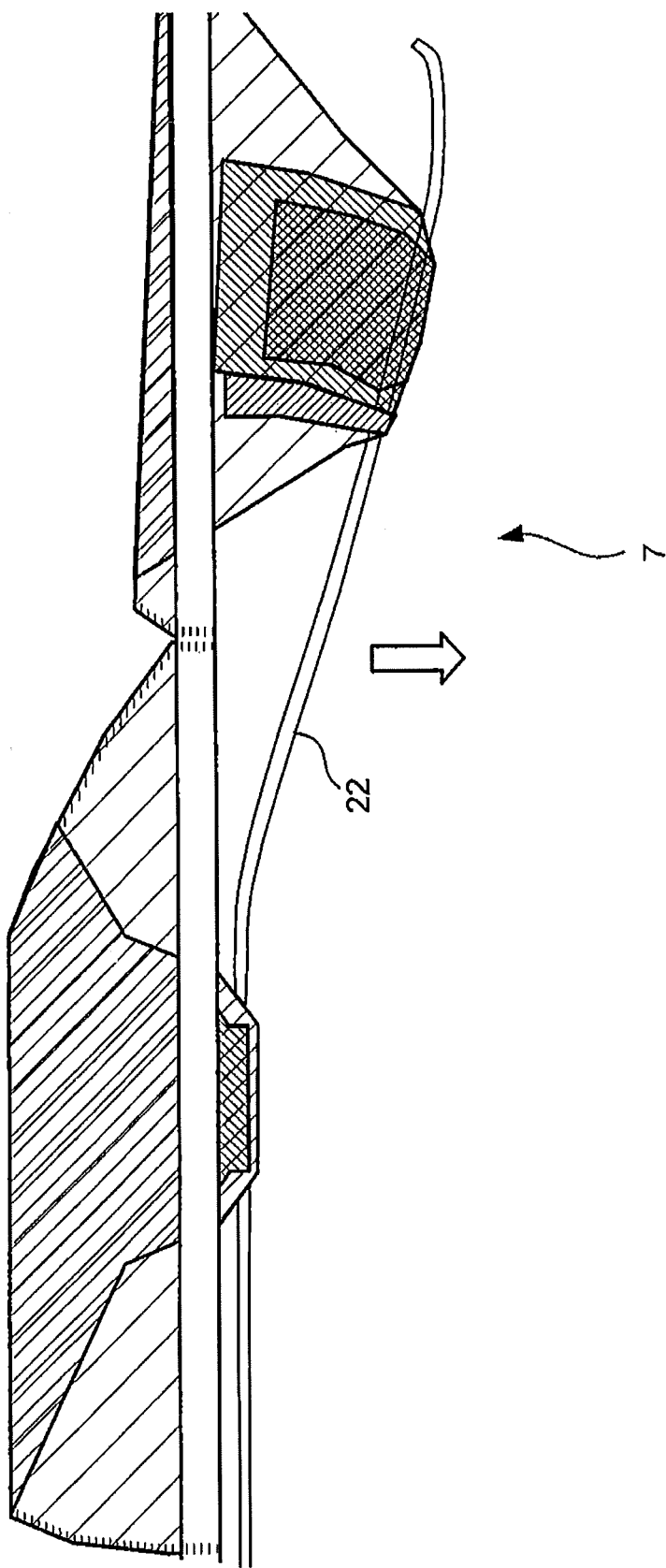

In FIG. 10, the third folding process at the third folding means 7 is shown, wherein the first guide bar 22 simply bends away from its original path, such as to pull downwards the crotch section of the absorbent article, such that the material folded in the second folding action is actually reversed with respect to its orientation.

Figure 11:
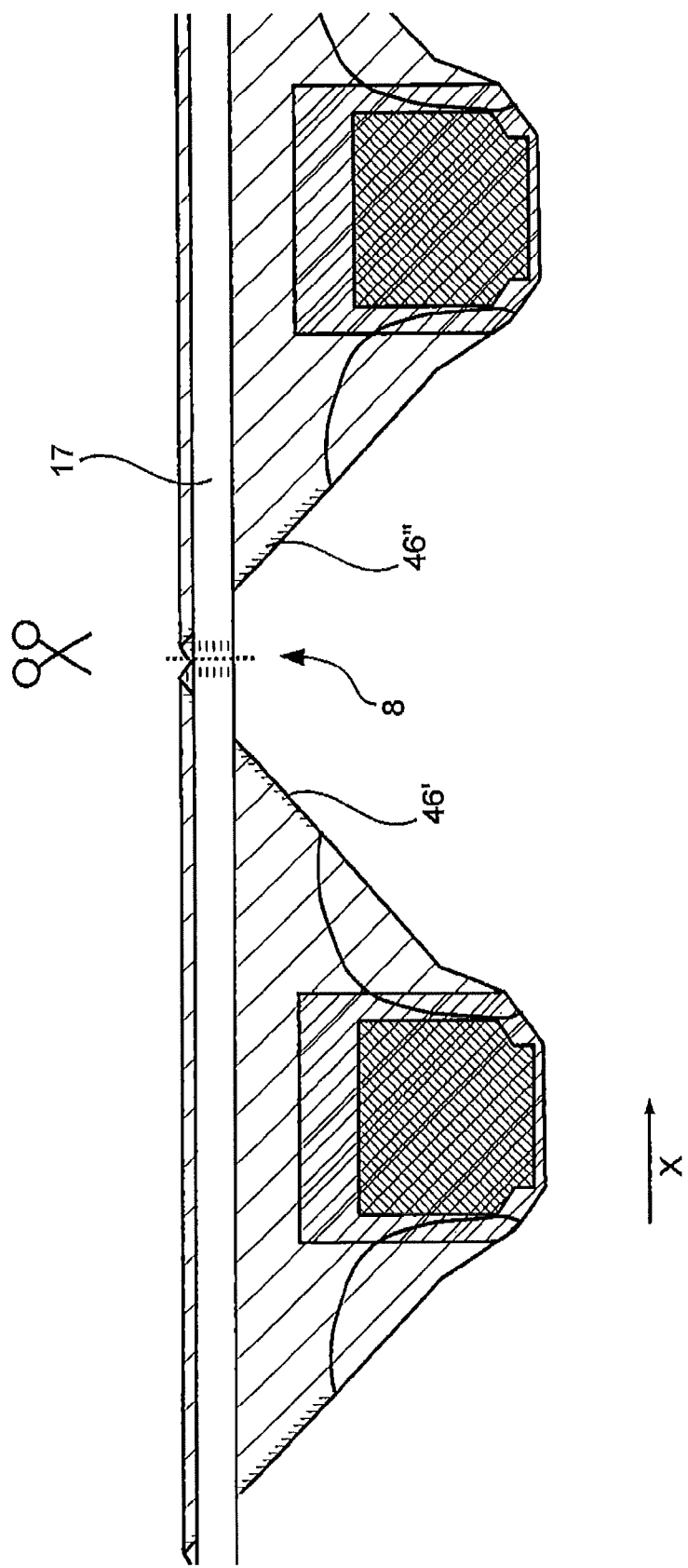

The resulting absorbent article is shown in FIG. 11, in which, at station 8, a final cut is carried out to separate individual absorbent articles from the web.

It is to be noted that the waist band 70 is still in the folded position as carried out in the second folding step. However, the majority of the joint 46' and 46" is folded back so that the flange material situated between the first seam 46' and the second seam 46" actually points towards the inside.

Figure 12:
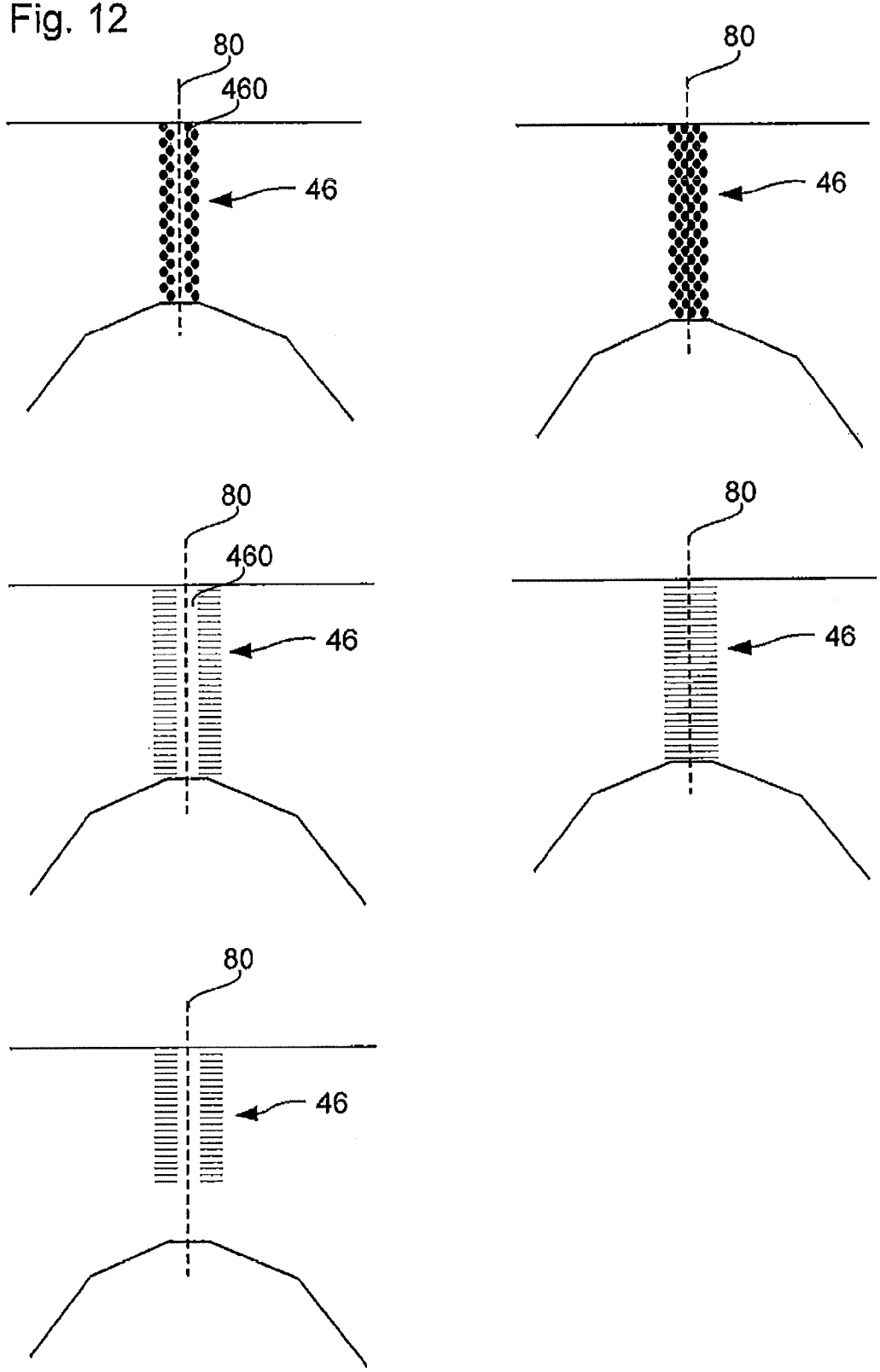
FIG. 12 shows different variants of joints in the product.

FIG. 12 shows different variants of forming a joint 46. In particular, the joints at the right hand side of the Figure are provided in the form of full joints in which a relatively large area of the web is joined together. The joints 46 shown on the left hand side of the Figure are provided in the form of separated welding spots which are situated more or less symmetrical to the intended separating line 80 such that unbonded material remains in the flange portions 460. This unbonded material in the flange portions 460 has the advantage that the joints have a softer feel to the skin.

Figure 13:
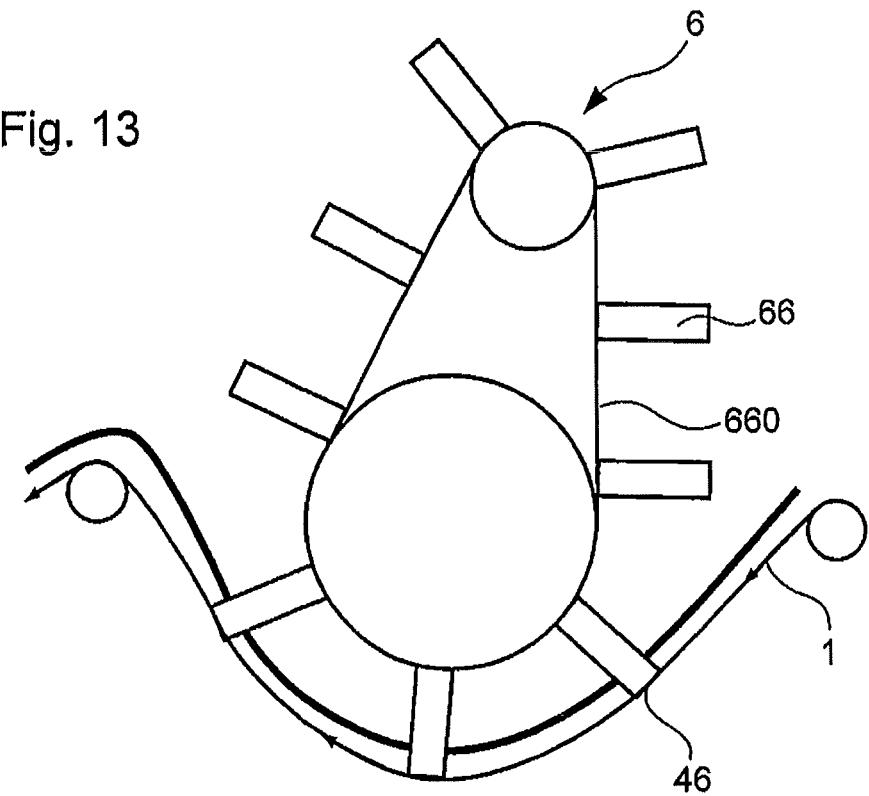
FIG. 13 shows an alternative embodiment of a holding means.

FIG. 13 shows an alternative to the polygonal wheel 62 shown in FIG. 3. Here, the web 1 is held at the respective joints by means of paddles 66 which are driven on a chain belt 660.

Figure 14:
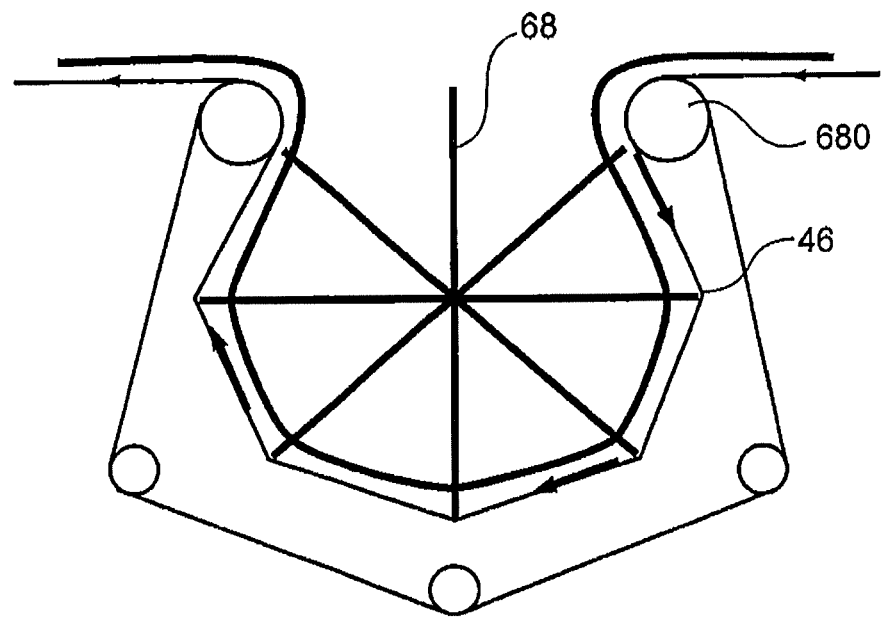
FIG. 14 shows yet another embodiment of a holding means.

FIG. 14 shows yet another embodiment of a holding means 6, namely in the form of paddles 68 which press against a conveyer belt 680 at the positions of the respective joints 46.

Figure 15:
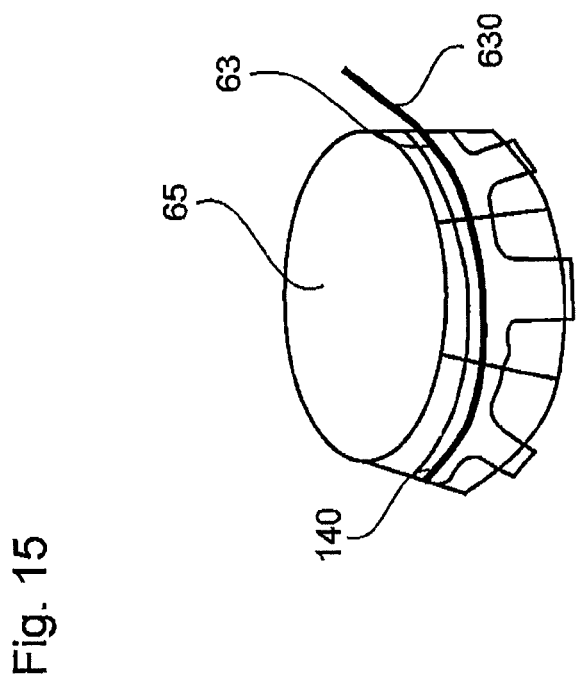
FIG. 15 shows another variant of a holding means.

As shown in FIG. 15, in order to ensure a secure conveying during the third folding process, a groove 63 can be provided in a substantially round wheel 65, wherein in the groove 63 the waist band portion 140 can be situated while the third folding action is carried out. The waist band portion 140 may be pressed into the groove 63 by means of a holding belt 630 which is situated substantially in the same position as the groove 63 and presses the waist band portion 140 towards the wheel 65.

Figure 16:
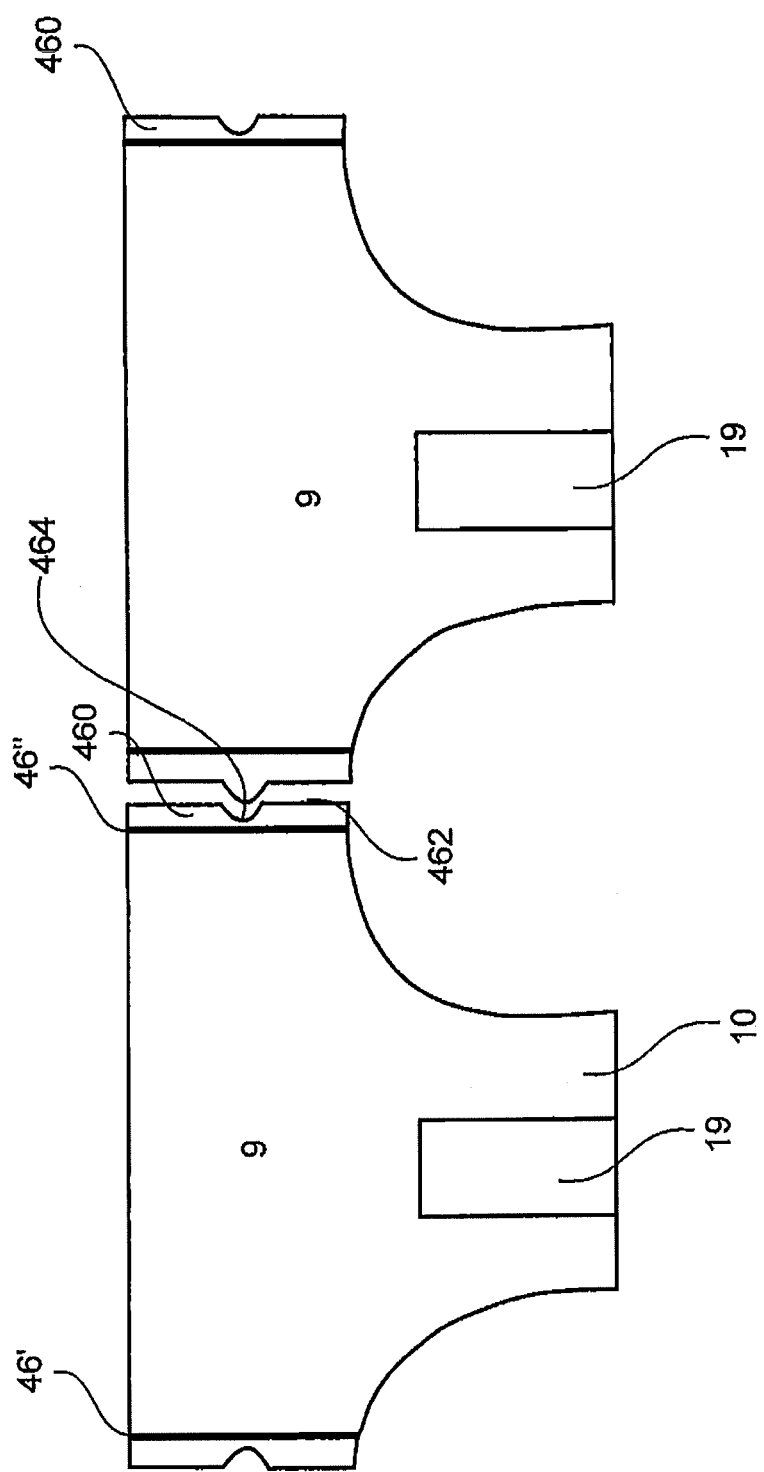
FIG. 16 shows an absorbent article manufactured by the method.

In FIG. 16, an individual absorbent article 9 is shown, in its reversed state such that the absorbent core 19 points towards the outside and it is the first side 10 that points towards the outside. The two seams 46' and 46" are shown, which leave flange material 460 remaining at the outside. This flange material 460 points towards the inside of the pant when it is in its final arrangement.

Because a first separation step and a second separation step are carried out at two consecutive absorbent articles, the cut at the flange 460 shows an irregular edge 462 which may have kinks 464 in it. Furthermore, the absorbent article shown on the right-hand side of FIG. 16 shows an asymmetric irregularity on its left- and right-hand sides of flange 460.

Figure 17:
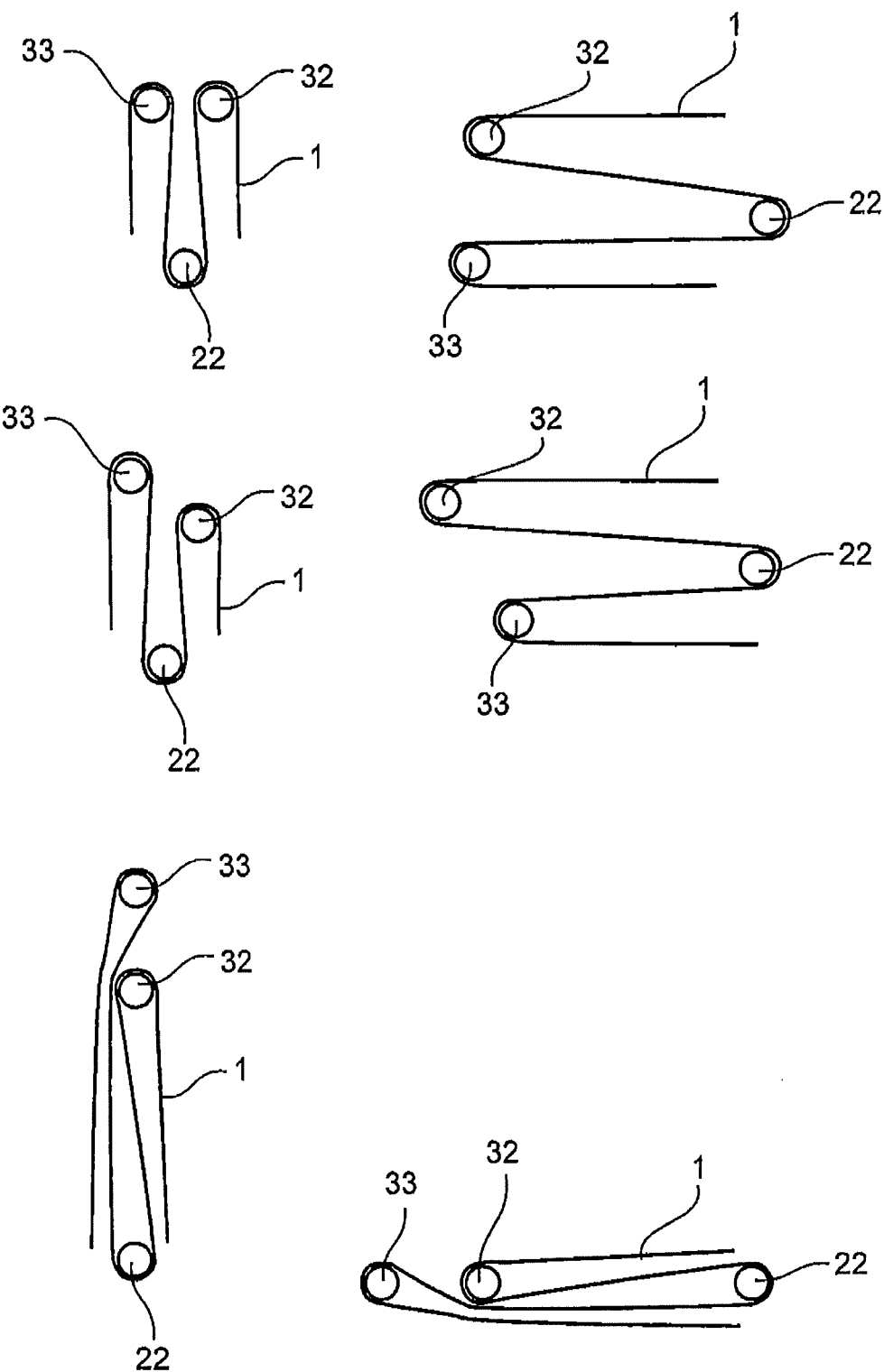
FIG. 17 shows different arrangements of the first and second guide bars.

FIG. 17 shows exemplarily cross sections through the arrangement of the first guide bar 22 and the second guide bars 32, 33 in different arrangements. It is noted that the distance between the first guide bar 22 and the respective third guide bars 32, 33 is determined, inter alia, by the lateral distance of the margins 18. This dimensional restriction is necessary in order to carry out the joining step by means of the welding horn 42 as shown in FIG. 1 such that only two layers of the material are joined to one another, substantially through the opening 16.

In fact, in order to be in a position to carry out the method shown schematically in FIG. 1, the maximum lateral size of the opening 16 has to be larger than two times the smaller of the margins 18. Typically, the margins 18 have the identical lateral extension such that the opening 16 needs to be larger at the position in which the joint is to be formed than twice the lateral extension of the margins 18.

The different arrangements shown in FIG. 17 do not only accommodate for asymmetric shapes of the opening 16 such as to provide larger coverage of the disposable pants at the back side than at the front side, but also accommodate for different arrangements of the apparatus.

Figure 18:
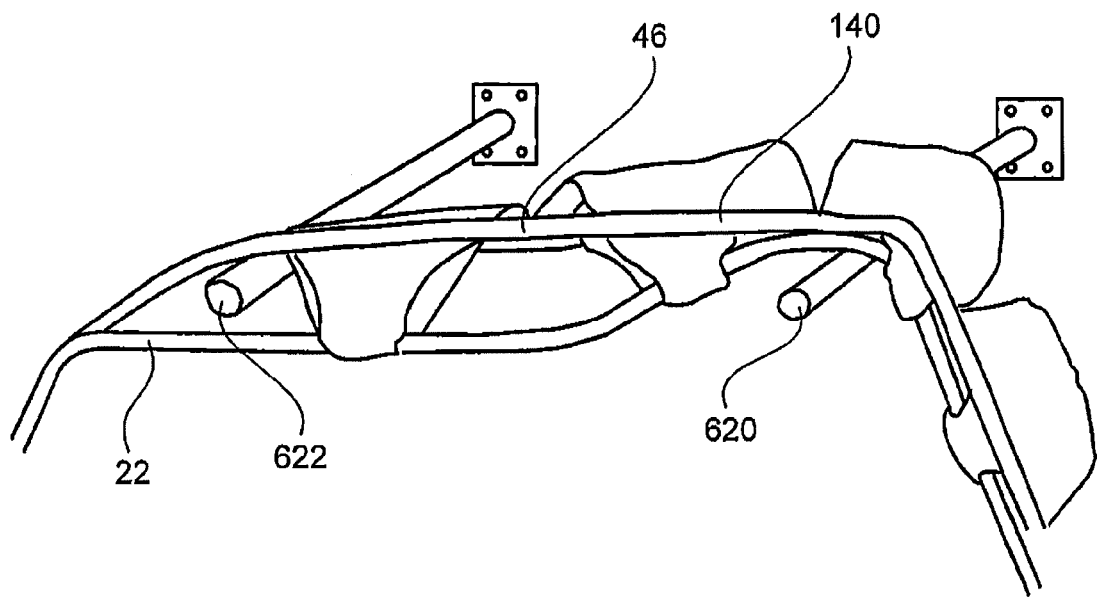
FIG. 18 shows an alternative embodiment for carrying out the third folding action.

FIG. 18 shows yet another embodiment of an apparatus for carrying out the third folding action. In particular, the absorbent article is still guided by the first guide bar 22 at its crotch portion and the waist band portion 140 is guided by two rollers 620, 622. In order to carry out the third folding action, namely to unfold the pants, the first guide bar 22 is guided away from the plane in which the waist band portion 140 of the absorbent article is guided and held by the two rollers 620, 622 such that the third folding action is carried out and the crotch portion is unfolded such that the seams at the joints are turned at least partially towards the inside of the final pants.

The invention claimed is:

1. A method of manufacturing absorbent articles, the method comprising:
feeding a longitudinal web of web material, the web having two opposing longitudinal edges, a first side and a second side, the web furthermore having openings situated between the two opposing longitudinal edges, the openings being spaced apart from one another in the longitudinal direction of the web such that spaced apart, opposing margins of web material are formed between the respective opening and the opposing longitudinal edges of the web material;
carrying out a first folding action of folding the web about itself along the longitudinal direction such that portions of the first side of the web face each other;
carrying out a second folding action of folding at least a portion of the web along the longitudinal direction to bring together the opposing margins of web material such that the opposing margins face each other on the second side of the web;
after the second folding action, forming a joint in the web, the joint being formed at least in a part of a region in which the opposing margins have been brought together by the second folding action, the joint extending between the longitudinal edges and the opening in the web carrying out a third folding action of at least partially reversing the second folding action such that at least portions of the web folded in the second folding action face each other on the first side of the web, and holding the web when carrying out the third folding action; and
finally separating the web through the joint to separate an individual absorbent article from the end of the web.

2. The method according to claim 1, the method after forming the joint further comprises the step of pre-separating the web in the region where the joint is formed while leaving at least a portion of the margins unaffected to maintain integrity of the web along the longitudinal direction, the unaffected portion of the margins extending towards the longitudinal edges.

3. The method according to claim 1, further comprising the step of folding the web in the first folding action substantially about a longitudinal center line of the web.

4. The method according to claim 1, further comprising the step of folding the web in the first folding action substantially about a folding line which is offset from a longitudinal center line of the web.

5. The method according to claim 1, wherein in the second folding action the web is folded about a line which is spaced apart from the respective longitudinal edges of the web substantially by width of one of the margins of the unfolded web.

6. The method according to claim 1, wherein the two opposing longitudinal edges of the web are aligned with one another in or after the second folding step.

7. The method according to claim 1, wherein the two opposing portions are folded phase shifted sequentially, in the second folding step.

8. The method according to claim 1, wherein in the step of forming a joint, the joint is provided in the form of two or more separate joining portions.

9. The method according to claim 8, wherein the two or more separate joining portions are provided sequentially.

10. The method according to claim 1, further comprising the step of, before the first folding action, providing the web with absorbent sections spaced apart in the longitudinal direction on the first side of the web, the absorbent section being situated between two respective openings.

11. The method of claim 1, wherein the absorbent articles are disposable diaper pants or disposable incontinence pants.

* * * * *